(12) United States Patent
Madhavi et al.

(10) Patent No.: US 8,435,967 B2
(45) Date of Patent: May 7, 2013

(54) WATER DISPERSIBLE POLICOSANOL CYCLODEXTRIN COMPLEX AND METHOD OF ITS PRODUCTION

(75) Inventors: Doddabele L. Madhavi, Worcester, MA (US); Daniel I. Kagan, Belmont, MA (US)

(73) Assignee: Bio-Actives LLC, Worcester, MA (US)

( * ) Notice: Subject to any disclaimer, the term of this patent is extended or adjusted under 35 U.S.C. 154(b) by 37 days.

(21) Appl. No.: 12/957,525

(22) Filed: Dec. 1, 2010

(65) Prior Publication Data
US 2011/0071110 A1      Mar. 24, 2011

Related U.S. Application Data

(62) Division of application No. 12/070,195, filed on Feb. 15, 2008, now abandoned.

(60) Provisional application No. 60/901,533, filed on Feb. 15, 2007.

(51) Int. Cl.
*A61K 31/724* (2006.01)
*A61K 31/045* (2006.01)

(52) U.S. Cl.
USPC ............................... 514/58; 514/724; 426/648

(58) Field of Classification Search .................. None
See application file for complete search history.

(56) References Cited

U.S. PATENT DOCUMENTS

2003/0232796 A1* 12/2003 Cooper et al. ................ 514/169

OTHER PUBLICATIONS

STN abstract of CN 1698586 (2005).*
Machine translation of CN 1698586 (2005).*
Translation of Chen et al, CN 1698586 (2005).*
Loftsson, T. et al "Cyclodextrins and their pharmaceutical applications" (2007) vol. 329, pp. 1-11.*

* cited by examiner

*Primary Examiner* — Leigh Maier
(74) *Attorney, Agent, or Firm* — Mueller Law, LLC; Jerry K. Mueller, Jr.

(57) ABSTRACT

Disclosed is a formulation of policosanol with natural cyclodextrins resulting in a water dispersible form of policosanol. The disclosed process provides an economical commercial method for making the policosanol complex. The complex is suitable for incorporation into oral dosage forms and also in functional foods. One aspect of the present disclosure is a process for making a water dispersible policosanol cyclodextrin complex for animal ingestion. This method includes preparing a policosanol cyclodextrin complex and administering said complex to an animal. The preferred animal is a human with the route of administration being oral ingestion. The form of the complex for ingestion can be a hard gelatin capsule, tablet or wafers, which may contain other ingredients, both active and inactive. The complex also can be further formulated with excipients suitable for soft gelatin capsules, such as, for example, vegetable oils, waxes, lecithin, and surfactants such as Tween-80.

9 Claims, 3 Drawing Sheets

WATER DISPERSIBLE POLICOSANOL CYCLODEXTRIN COMPLEX AND METHOD OF ITS PRODUCTION

CROSS-REFERENCE TO RELATED APPLICATIONS

This application is a divisional application of U.S. Ser. No. 12/070,195, filed Feb. 15, 2008, the disclosure of which is expressly incorporated herein by reference This application claims benefit of provisional application Ser. No. 60/901,533 filed on Feb. 15, 2007, the disclosure of which is expressly incorporated herein by reference.

STATEMENT REGARDING FEDERALLY SPONSORED RESEARCH

Not applicable.

BACKGROUND

The present disclosure generally relates to development of water dispersible policosanol-cyclodextrin complexes for use in nutritional supplements and functional foods.

Cyclodextrins (sometimes abbreviated herein as "CD" or "CD's") are cyclic oligosaccharides composed of 6, 7, or 8 α-(1-4)-linked anhydroglucose units. The α-, β-, and γ-cyclodextrins prepared from starch are considered natural and are GRAS according to the USFDA. The cyclodextrins are widely used in the pharmaceutical industry to improve dissolution, stability and uptake of lipophilic molecules.

Policosanol is a complex mixture of lipophilic very long-chain alcohols ($C_{24}$-$C_{34}$) isolated from waxes, such as, for example, sugarcane wax, rice bran wax, or beeswax. Typical commercially available policosanol contains 90% minimum fatty alcohols. The content of individual alcohols vary based on the source of wax and the process of isolation. The fatty alcohols in policosanol are primarily tetracosanol (0.5%-10%), hexacosanol (2%-15%), octacosanol (20%-70%), and triacontanol (5%-20%), while eicosanol, docosanol, heptacosanol, nonacosanol, dotriacontanol, tetratriacontanol, and hexatriacontanol make up the remaining minor constituents.

Policosanol is used as a natural supplement to lower total cholesterol and low-density lipoproteins and raise high-density lipoproteins. Policosanol is a highly lipophilic material, insoluble in water and has poor bioavailability in humans. Policosanol has been reported to reduce cholesterol synthesis in vitro in cell cultures (Singh, D K, Li, L, and Porter, T D, Policosanol inhibits cholesterol synthesis in hepatoma cells by activation of AMP-kinase, *J Pharmacol Exp Ther.* 2006, 318:1020-6; Menendez R, Amor A M, Rodeiro I, Gonzalez R M, Gonzalez P C, Alfonso J L, Mas R, Policosanol modulates HMG-CoA reductase activity in cultured fibroblasts, *Arch Med Res.* 2001, 32:8-12). However, in human studies the results have been variable with minimal uptake of policosanol. It has been suggested that the lower and variable efficacy of poilcosanols in human studies can be due to their poor absorption from conventional delivery systems used in the industry. Hence it is desirable to develop an effective delivery system, which is commercially feasible in a cost sensitive supplement industry.

BRIEF SUMMARY

The present disclosure is a formulation of policosanol with natural cyclodextrins resulting in a water dispersible form of policosanol, thereby improving bioavailability. The disclosed process provides an economical commercial method for making the policosanol complex. The complex is suitable for incorporation into oral dosage forms and also in functional foods.

One aspect of the present disclosure is a process for making a water dispersible policosanol cyclodextrin complex for animal ingestion. This method includes preparing a policosanol cyclodextrin complex and administering said complex to an animal. The preferred animal is a human with the route of administration being oral ingestion. The form of the complex for ingestion can be a hard gelatin capsule, tablet or wafers, which may contain other ingredients, both active and inactive. The complex also can be further formulated with excipients suitable for soft gelatin capsules, such as, for example, vegetable oils, waxes, lecithin, and surfactants such as, for example, Tween-80.

BRIEF DESCRIPTION OF THE DRAWINGS

For a fuller understanding of the nature and advantages of the present invention, reference should be had to the following detailed description taken in connection with the accompanying drawings, in which.

Figure 1:
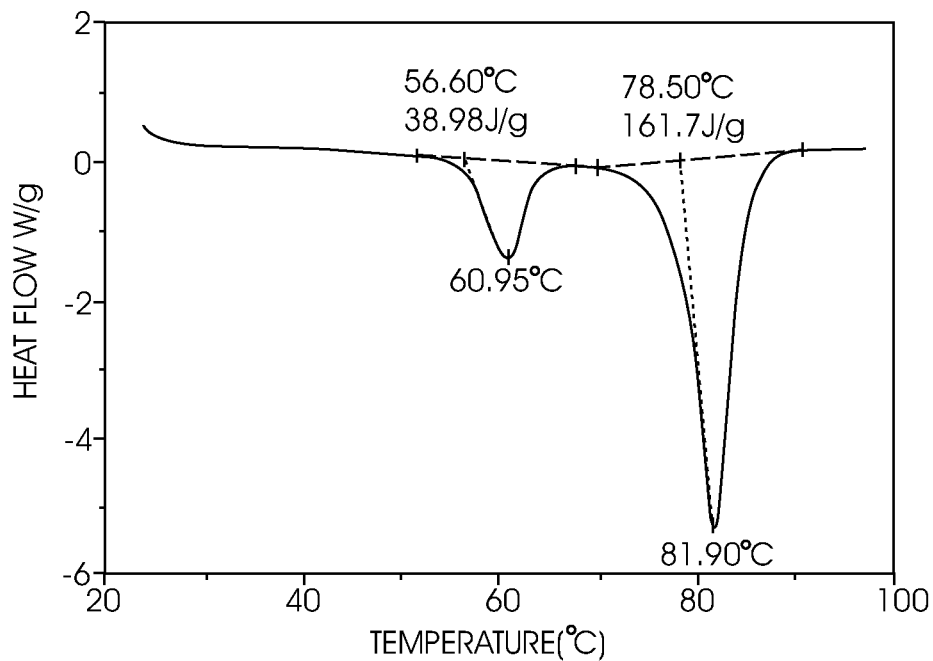
FIG. 1 represents the DSC profile of free Policosanol.
Figure 2:
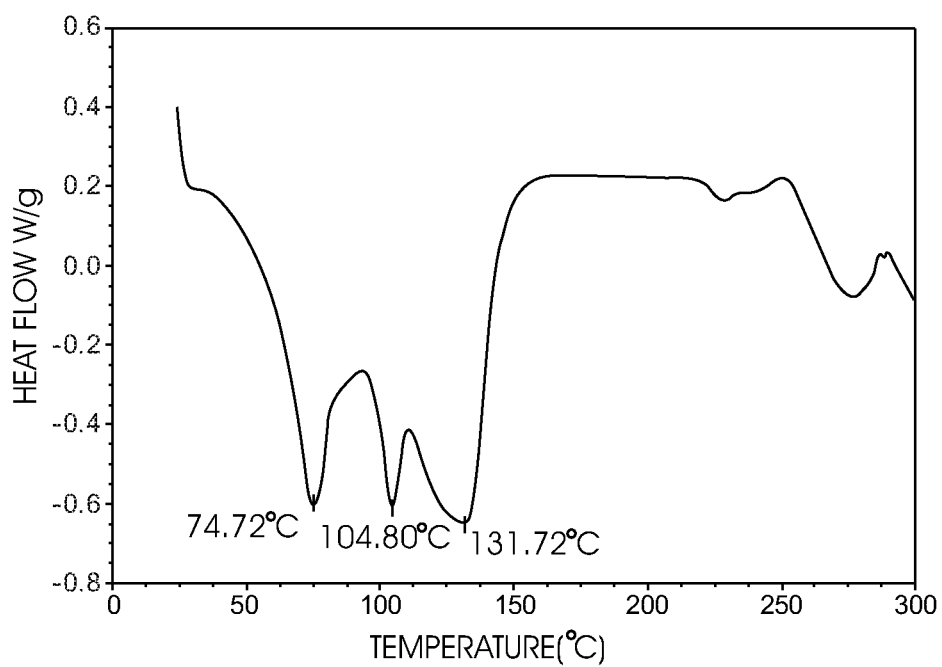
FIG. 2 represents the DSC profile of alpha-CD.
Figure 3:
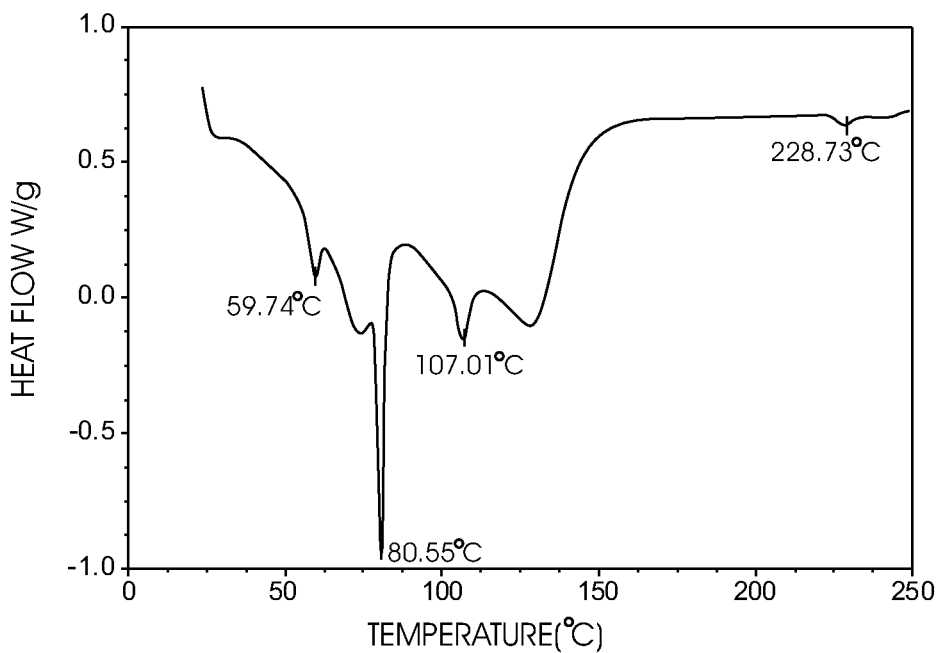
FIG. 3 represents the DSC profile of physical mixture of alpha-CD+Policosanol.
Figure 4:
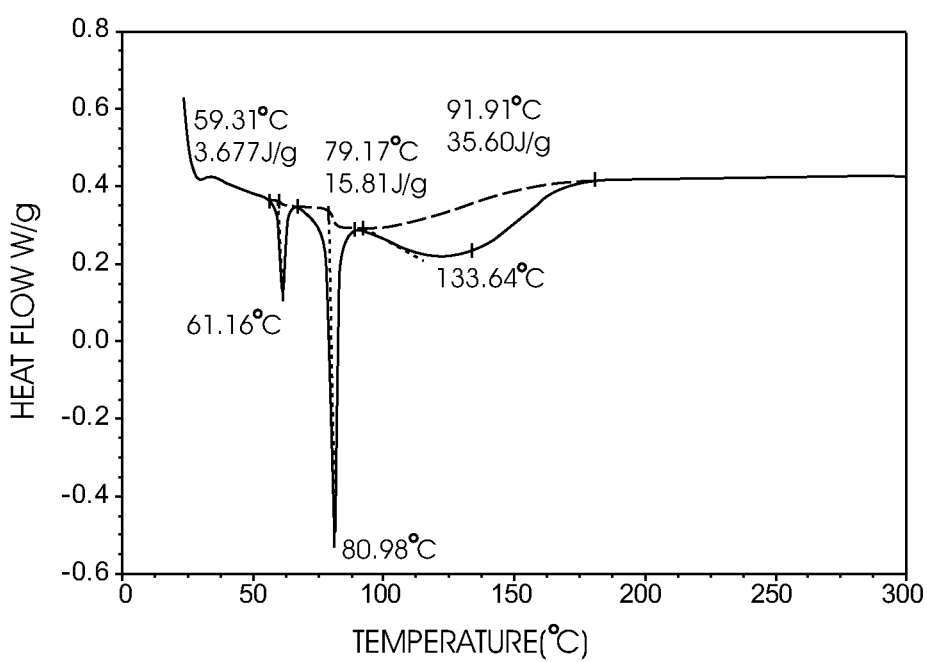
FIG. 4 represents the DSC profile of alpha-CD Policosanol complex.

The drawings will be described in further detail in the examples below.

DETAILED DESCRIPTION

The present disclosure describes a method for making a water dispersible form of policosanol complexed with α-, β- or γ-cyclodextrin for use in the nutritional supplement, food, and pharmaceutical industry. Commercially available policosanol from sugarcane, rice bran, and beeswax containing 20%-70% Octacosanol was used for complexation. The molecular weight of Octacosanol was used to calculate the molar ratio. The molar ratio of cyclodextrin to policosanol can range, for example, from about 0.5:1 to about 10:1, and preferably from about 1:1 to about 2:1 for commercial production. The policosanol concentration in the complex can range, for example, from about 3% to about 40% (w/w). The policosanol/cyclodextrin complex (1:2 molar) was prepared using an aqueous slurry method. Policosanol was mixed with a non-ionic surfactant, such as, for example, Tween-80. The amount of surfactant can range between about 0.1% to about 15% by weight of policosanol, preferably between about 10% and about 15%. Heating to 70° C. melted the mixture. The cyclodextrin was dissolved in water (1:6 w/v) by heating to 70° C. The policosanol surfactant mixture was added to the cyclodextrin solution under high-speed homogenization using a Silverson high shear mixer. The complex started to precipitate out of solution after about 20 to about 30 minutes. The solution was allowed to come to room temperature and stirred overnight using an overhead stirrer. The properties of the complex can be further improved by the addition of, for example, bioadhesive polymers to the slurry before drying. The slurry can be dried by any commercial drying methods such as, for example, freeze-drying, spray-drying, or vacuum-drying.

The aqueous slurry was dried by freeze-drying using a semi-commercial tray freeze dryer (Virtis). The product obtained was a white free flowing powder suitable for capsules, tablets, and/or further formulation compounding. The dried product can be micronized or ground and/or sieved to form a uniform powder suitable for further applications or formulations.

The interaction of cyclodextrins with policosanol and the quantification of amount of policosanol complexed were determined by Differential Scanning Calorimetry (DSC) and Thermo Gravimetric Analysis (TGA). The DSC is based on the disappearance of the melting peak or a reduction in the melting peak area of the guest molecule. The amount of complexation can be calculated based on the melting peak area of the guest molecule before and after complexation. The TGA gives an indication of the interaction between the guest and cyclodextrins. The complex may be more thermo stable as compared to the free guest molecule or a physical mixture of the guest and cyclodextrin. The techniques have been widely used to study the complexation of cyclodexrins with various guest molecules (Rossel, C. P., Carreno, J. S., Rodriguez-Baeza, M., and Alderete, J. B., Inclusion complex of the antiviral drug acyclovir with cyclodextrin in aqueous solution and in solid phase, Quimica Nova, 23(6): 749-752, 2000; Zuo, Z., Kwon, G., Stevenson, B., Diakur, J., and Wiebe, L. I., J. Pharm. Pharmceut Sci., Flutamide-hydroxypropyl-beta-cyclodextrin complex: Formulation, physical characterization and absorption studies using the Caco-2 in vitro model, 3(2): 220-227, 2000).

While the water dispersible policosanol cyclodextrin complex has been described with reference to various embodiments, those skilled in the art will understand that various changes may be made and equivalents may be substituted for elements thereof without departing from the scope and essence of the disclosure. In addition, many modifications may be made to adapt a particular situation or material to the teachings of the disclosure without departing from the essential scope thereof. Therefore, it is intended that the water dispersible policosanol cyclodextrin complex not be limited to the particular embodiments disclosed, but that the water dispersible policosanol cyclodextrin complex will include all embodiments falling within the scope of the appended claims. In this application all units are in the metric system and all amounts and percentages are by weight, unless otherwise expressly indicated. Also, all citations referred herein are expressly incorporated herein by reference.

EXAMPLES

Example 1

51 g alpha-CD was dissolved in 300 ml of water by heating to 70° C. 10 g of sugarcane Policosanol was mixed with 1.5 g of Tween-80 (also known as Polysorbate 80, is a mixture oleate esters of sorbitan polyethoxylates) and melted by heating to 70° C. The oily mixture was added to the CD solution under homogenization. After 30 min of homogenization, the complex started to precipitate out of solution. The mixture was cooled to room temperature and stirred overnight using an overhead stirrer. The slurry was freeze-dried to obtain a white water dispersible powder containing 16% policosanol.

Figure 5:
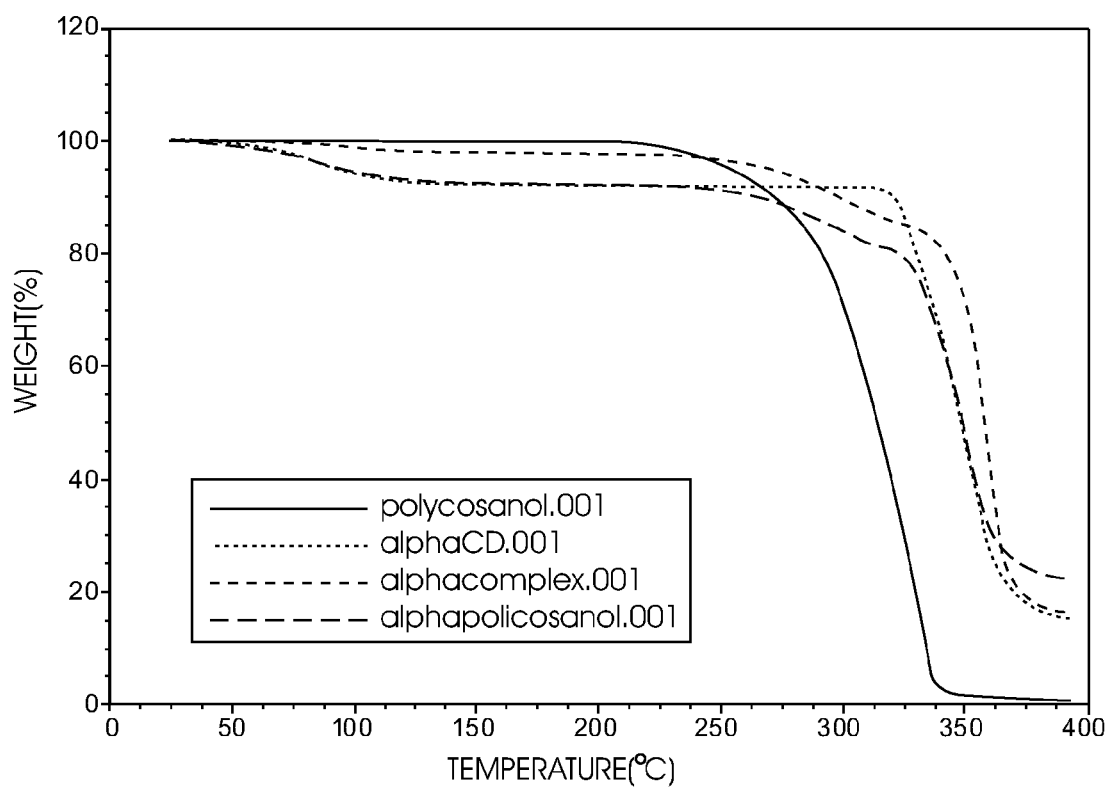
FIG. 5 represents the TGA overlay of Policosanol, alpha-CD, Physical mixture and the complex.

The DSC analysis was conducted using TA Instruments 2920 in an inert atmosphere. FIGS. 1-4 present the DSC profiles of Policosanol, alpha-CD, policosanol+alpha-CD physical mixture and the complex respectively. Policosanol showed a major melting endotherm at 81.9° C. The area of the endotherm, which is proportional to the free Policosanol, makes it possible to quantify the complexing. Policosanol delta-H=156.4 j/g; uncomplexed Policosanol in complex delta-H=15.70 j/g. Uncomplexed Policosanol, 10%. FIG. 5 presents the TGA overlay of Policosanol, alpha-CD, policosanol+alpha-CD physical mixture and the complex. The complex showed more thermal stability than the free Policosanol and the physical mixture.

Example 2

62 g beta-CD was dissolved in 300 ml of water by heating to 70° C. 10 g of sugarcane Policosanol was mixed with 1.5 g of Tween-80 and melted by heating to 70° C. The oily mixture was added to the CD solution under homogenization. After 30 min of homogenization, the complex started to precipitate out of solution. The mixture was cooled to room temperature and stirred overnight using an overhead stirrer. The slurry was freeze-dried to obtain a white water dispersible powder containing 14% policosanol. The DSC analysis indicated the uncomplexed Policosanol as 9%.

Example 3

69.5 g gamma-CD was dissolved in 300 ml of water by heating to 70° C. 10 g of sugarcane Policosanol was mixed with 1.5 g of Tween-80 and melted by heating to 70° C. The oily mixture was added to the CD solution under homogenization. After 30 min of homogenization, the complex started to precipitate out of solution. The mixture was cooled to room temperature and stirred overnight using a overhead stirrer. The slurry was freeze-dried to obtain a white water dispersible powder containing 12.5% policosanol. The DSC analysis indicated the uncomplexed Policosanol as 11%.

We claim:

1. A method for making a water dispersible complex, which comprises the steps of:
 (a) forming a heated oily solution of policosanol and a surfactant;
 (b) forming a heated aqueous solution of a cyclodextrin;
 (c) mixing said oily solution under homogenization with said aqueous cyclodextrin solution until formation of a complex precipitate; and
 (d) cooling said mixture under stirring for a time sufficient to complete said complex formation;
 (e) said cooled mixture is dried to recover a complex precipitate powder; wherein the amount of uncomplexed policosanol in said powder is 11% or less.

2. The method of claim 1, wherein the molar ratio of cyclodextrin to policosanol ranges from about 0.5:1 to about 10:1.

3. The method of claim 1, wherein said cyclodextrin is one or more of α-cyclodextrin, β-cyclodextrin, or γ-cyclodextrin.

4. The method of claim 1, wherein policosanol is an isolate from one or more of sugarcane was, rice bran wax, or beeswax.

5. The method of claim 1, wherein said surfactant in step (a) ranges from between about 0.1 wt-% and about 15 wt-% by the weight of the policosanol.

6. The method of claim 5, wherein said surfactant comprises a non-ionic surfactant.

7. The method of claim 6, wherein said surfactant is polysorbate 80.

8. The method of claim 1, wherein said complex precipitate is recovered as a powder by drying.

9. The method of claim 8, wherein said drying comprises one or more of freeze-drying, spray-drying, or vacuum-drying.

\* \* \* \* \*